(12) United States Patent
Hestad et al.

(10) Patent No.: US 7,799,079 B2
(45) Date of Patent: Sep. 21, 2010

(54) VERTEBRAL FUSION DEVICE AND METHOD

(75) Inventors: Hugh D. Hestad, Edina, MN (US); Jack Maertens, Chaska, MN (US); Bruce Robie, Glen Rock, NJ (US); Robert Garryl Hudgins, Burnsville, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 369 days.

(21) Appl. No.: 11/334,326

(22) Filed: Jan. 18, 2006

(65) Prior Publication Data

US 2007/0173940 A1 Jul. 26, 2007

(51) Int. Cl.
*A61F 2/44* (2006.01)
*A61B 17/88* (2006.01)

(52) U.S. Cl. .................... 623/17.12; 606/279

(58) Field of Classification Search .......... 623/17.11, 623/17.12, 17.15, 17.16
See application file for complete search history.

(56) References Cited

U.S. PATENT DOCUMENTS

| | | | |
|---|---|---|---|
| 3,867,728 A * | 2/1975 | Stubstad et al. ........... | 623/17.16 |
| 5,549,679 A | 8/1996 | Kuslich | |
| 5,571,189 A | 11/1996 | Kuslich | |
| 5,681,310 A | 10/1997 | Yuan et al. | |
| 6,093,205 A | 7/2000 | McLeod et al. | |
| 6,159,244 A | 12/2000 | Suddaby | |
| 6,174,334 B1 | 1/2001 | Suddaby | |
| 6,183,517 B1 | 2/2001 | Suddaby | |
| 6,332,894 B1 | 12/2001 | Stalcup et al. | |
| 6,332,895 B1 | 12/2001 | Suddaby | |
| 6,336,930 B1 * | 1/2002 | Stalcup et al. ............. | 606/284 |
| 6,391,060 B1 | 5/2002 | Ory et al. | |
| 6,395,032 B1 | 5/2002 | Gauchet | |

(Continued)

FOREIGN PATENT DOCUMENTS

DE 10052008 C1 8/2002

(Continued)

OTHER PUBLICATIONS

European Patent Office, Search Report and Written Opinion received in corresponding PCT application PCT/US2006/062087, dated Apr. 5, 2007, 11 pg.

*Primary Examiner*—Eduardo C Robert
*Assistant Examiner*—Ellen C Hammond
(74) *Attorney, Agent, or Firm*—Crompton, Seager & Tufte LLC (57) ABSTRACT

A device for facilitating bone fusion of two vertebrae. The device is sized and shaped to at least extend between the two vertebrae to be fused, and includes an outer wall member disposed about an inner portion. A space between the outer wall member and the inner compartment is adapted to contain an osteogenic bone fusion material. The inner portion includes a compartment adapted to contain an inner fill material, such as a bone cement or an in situ curable polymer. The inner portion may operate as a structural member to maintain a desired amount of spacing between the vertebrae to be fused, and to support the spinal column prior to formation of the fused bone joint. The device is also configured to locate the osteogenic material away from the centers of the vertebrae to be fused, providing a fused joint with high bending and torsional rigidity.

22 Claims, 11 Drawing Sheets

U.S. PATENT DOCUMENTS

| | | |
|---|---|---|
| 6,395,034 B1 | 5/2002 | Suddaby |
| 6,520,991 B2 | 2/2003 | Huene |
| 6,562,073 B2 | 5/2003 | Foley |
| 6,582,466 B1 * | 6/2003 | Gauchet .................. 623/17.11 |
| 6,709,458 B2 * | 3/2004 | Michelson ............... 623/17.15 |
| 6,712,853 B2 | 3/2004 | Kuslich |
| 6,726,721 B2 * | 4/2004 | Stoy et al. ................ 623/17.16 |
| 6,733,531 B1 | 5/2004 | Trieu |
| 6,733,533 B1 | 5/2004 | Lozier |
| 6,764,514 B1 | 7/2004 | Li et al. |
| 6,805,695 B2 | 10/2004 | Keith et al. |
| 6,827,743 B2 | 12/2004 | Eisermann et al. |
| 6,863,689 B2 | 3/2005 | Ralph et al. |
| 6,984,246 B2 * | 1/2006 | Huang ..................... 623/17.13 |
| 2002/0128715 A1 | 9/2002 | Bryan et al. |
| 2004/0249462 A1 | 12/2004 | Huang |
| 2005/0043733 A1 | 2/2005 | Eisermann et al. |
| 2005/0090901 A1 * | 4/2005 | Studer ..................... 623/17.12 |
| 2005/0107879 A1 * | 5/2005 | Christensen et al. ..... 623/17.11 |
| 2005/0113929 A1 | 5/2005 | Cragg et al. |
| 2005/0131536 A1 | 6/2005 | Eisermann et al. |
| 2005/0143825 A1 | 6/2005 | Enayati |
| 2005/0187627 A1 | 8/2005 | Ralph et al. |
| 2005/0209696 A1 * | 9/2005 | Lin et al. ................. 623/17.12 |
| 2005/0251259 A1 * | 11/2005 | Suddaby ................. 623/17.12 |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283244 A1 | 12/2005 | Gordon et al. |
| 2005/0283245 A1 | 12/2005 | Gordon et al. |
| 2005/0283246 A1 | 12/2005 | Cauthen, III et al. |
| 2005/0283247 A1 | 12/2005 | Gordon et al. |
| 2005/0283248 A1 | 12/2005 | Gordon et al. |
| 2007/0050033 A1 * | 3/2007 | Reo et al. ................. 623/17.12 |
| 2007/0093901 A1 * | 4/2007 | Grotz et al. .............. 623/17.11 |
| 2007/0093903 A1 * | 4/2007 | Cheng ..................... 623/17.12 |
| 2007/0100449 A1 * | 5/2007 | O'Neil et al. ............. 623/13.14 |
| 2007/0168042 A1 * | 7/2007 | Hudgins et al. .......... 623/17.16 |
| 2007/0250169 A1 * | 10/2007 | Lang ....................... 623/17.12 |

FOREIGN PATENT DOCUMENTS

EP         1132061 A2      9/2001

* cited by examiner

VERTEBRAL FUSION DEVICE AND METHOD

TECHNICAL FIELD

The present invention is related to spinal stabilization devices. More particularly, this invention relates to a device for facilitating the bony fusion of two vertebrae.

BACKGROUND

The spinal column is a highly complex system of bones and connective tissues that provides support for the body and protects the delicate spinal cord and nerves. The spinal column includes a series of vertebrae stacked one on top of the other, each vertebral body including an inner or central portion of relatively weak cancellous bone and an outer portion of relatively strong cortical bone. Between each vertebral body is an intervertebral disc that cushions and dampens forces experienced by the spinal column. A vertebral canal containing the spinal cord and nerves is located behind the vertebral bodies.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease, or trauma, such as ruptured or slipped discs, degenerative disc disease, fractured vertebra, and the like. Patients suffering from such conditions usually experience extreme and debilitating pain, as well as diminished nerve function. Such disorders can also limit range of movement and threaten the critical elements of the nervous system housed within the spinal column.

One well known method of treating certain spinal disorders via surgical intervention is to immobilize regions of the spine, usually by fusing or joining adjacent vertebrae to one another. A variety of techniques have been disclosed in the art for achieving this immobilization. One such fusion technique involves removal of all or part of the intervertebral disc between two vertebrae, and implanting a bone fusion mass or bone graft in the resulting space and in contact with the vertebral end plates. As a result, natural bone growth fuses the two vertebrae together. In a similar procedure, known as a corpectomy procedure, one or more vertebral bodies and adjacent intervertebral discs are removed and a bone graft is then implanted into the space between the vertebrae to be fused. Corpectomy is commonly utilized to treat spinal disorders in the cervical (i.e., neck) region, although it can also be effectively used in the middle and lower spinal regions.

The above-mentioned fusion techniques may require the implantation of one or more devices to facilitate implantation of the bone graft and to stabilize the patient's spinal column until the target vertebrae have been fused by natural bone growth.

Accordingly, there is a need in the art for a device to facilitate the formation of a strong bone fusion joint between adjacent vertebrae. Additionally, there is a need for such a device to facilitate the distraction of the vertebrae to be fused and to provide structural stability to the joint prior to formation of the fused bone joint.

SUMMARY

The present invention, in one embodiment, is an implantable orthopedic device for implantation between opposed vertebral end plates of a pair of vertebrae. The device includes an inner portion that has a pair of spaced-apart end caps and an inner wall member between the end caps, and an outer wall member disposed about and coupled to the inner portion. There is a separation between the outer wall member and the inner portion that defines an outer space. The device has a size and shape such that it can extend at least between the opposed vertebral end plates, such that at least the end caps can be in contact with the vertebral end plates and the outer space can be in communication with the vertebral end plates.

The present invention, in another embodiment, is a method of fusing a pair of vertebrae in a spine, including identifying a pair of vertebrae to be fused and removing a substantial portion of a disc between opposed vertebral end plates of the pair of vertebrae to be fused. A spacing between the pair of vertebrae to be fused is then created, and an implantable orthopedic device is inserted between the end plates. The device may include a compartment having first and second end caps, and a wall member wall member disposed about the compartment. There is a separation between the wall member and the compartment which defines an outer space. Next, a fill material is introduced into the compartment to longitudinally expand the compartment such that the end caps are in contact with the vertebral end plates. Then, an osteogenic material is introduced into the outer space such that the osteogenic material is in contact with the vertebral end plates.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
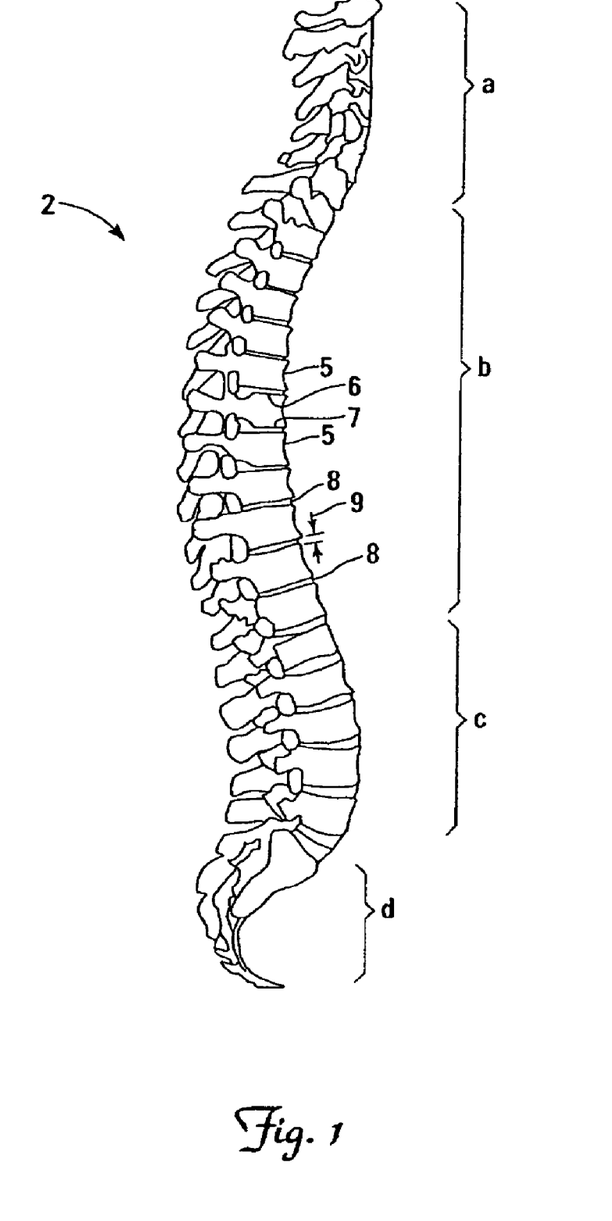
FIG. 1 illustrates a side view of a human spinal column.

FIG. 1 illustrates a human spinal column 2 including vertebrae 5 belonging to one of a cervical region a, a thoracic region b, a lumbar region c and a sacral region d of the spinal column 2. Each vertebra 5 includes a superior end plate 6 and an inferior end plate 7. Intervertebral discs 8 are positioned in intervertebral spaces 9 between adjacent vertebrae 5.

Figure 2:
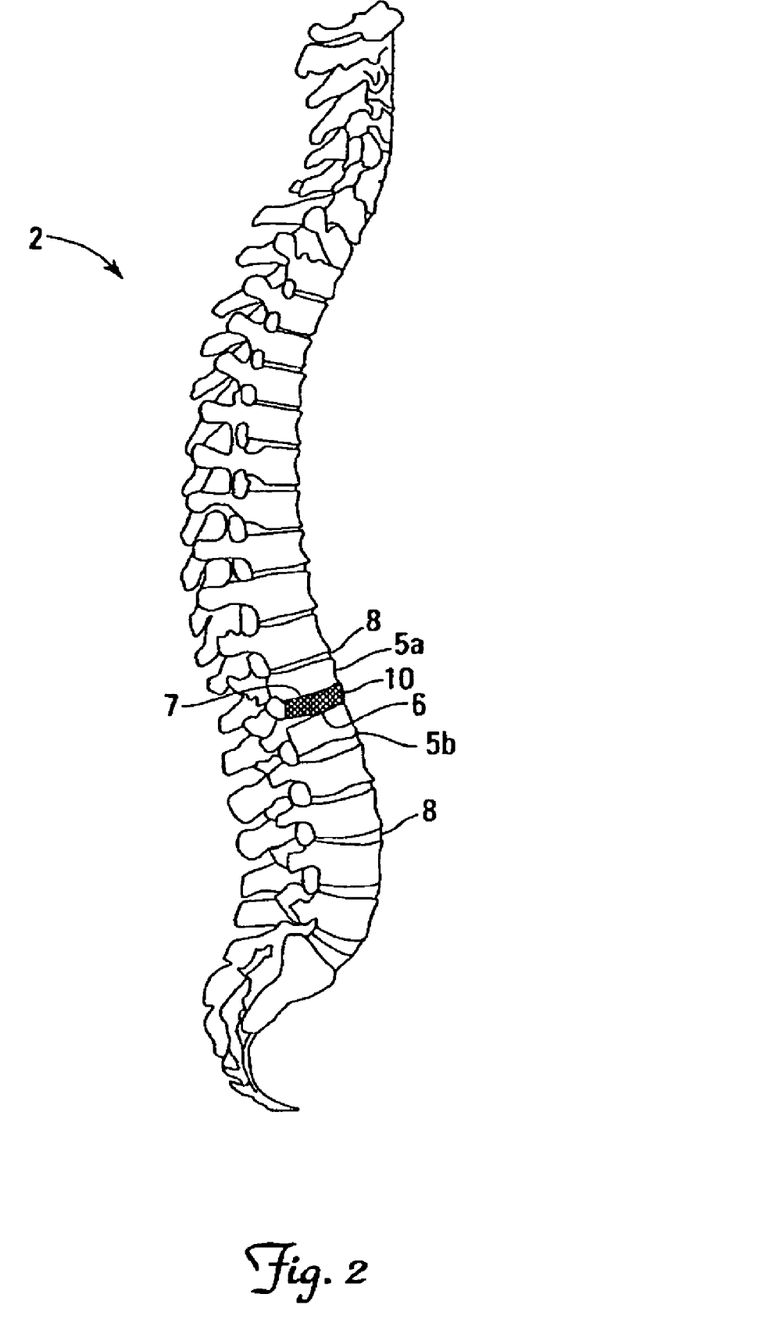
FIG. 2 illustrates a human spinal column in which an intervertebral disc has been removed and replaced with an implantable orthopedic device according to one embodiment of the present invention.

FIG. 2 illustrates a human spinal column 2 in which one of the discs 8 has been removed and replaced with an implantable orthopedic device 10 according to one embodiment of the present invention. As shown in FIG. 2, the device 10 generally occupies the same space as a natural disc 8 between the adjacent vertebrae 5a and 5b.

Figure 3:
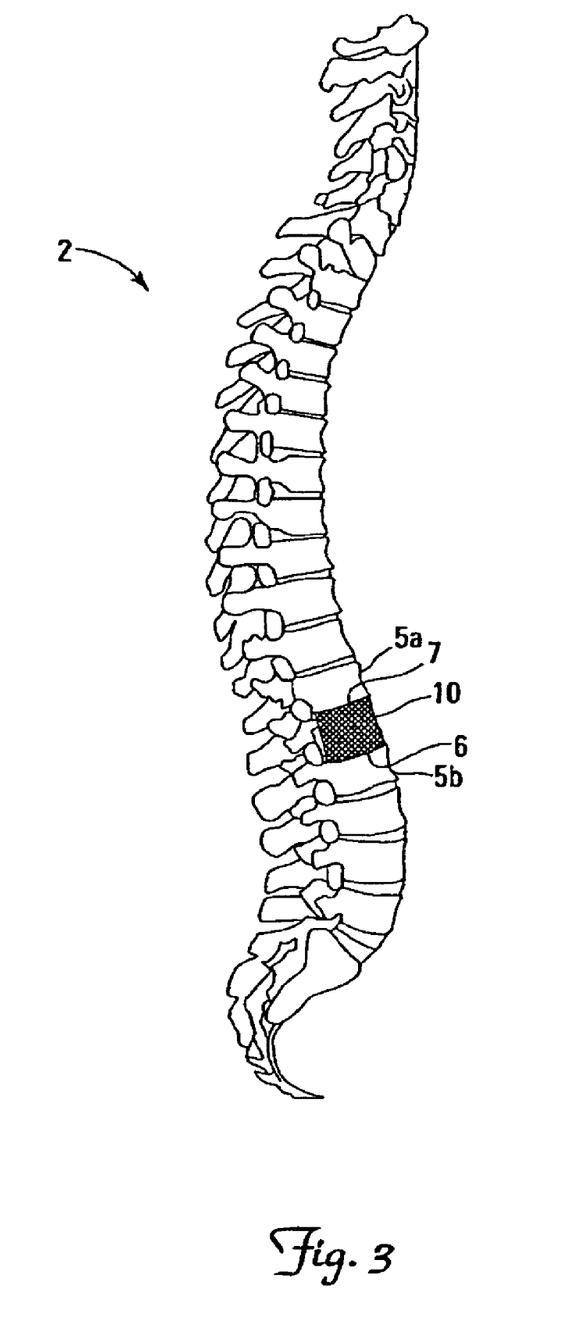
FIG. 3 illustrates a human spinal column in which a vertebra and adjacent discs have been removed, as in a corpectomy procedure, and replaced with an implantable orthopedic device according to one embodiment of the present invention.

FIG. 3 illustrates a human spinal column in which one of the vertebra 5 and the adjacent discs 8 have been removed and replaced with an implantable orthopedic device 10, as in a corpectomy procedure. As shown in FIG. 3, the device 10 generally occupies the same space as a natural vertebra/disc combination between the vertebrae 5a and 5b. Although in FIGS. 2 and 3 the device 10 is shown implanted into the lumbar region c, the device 10 is readily adapted in size and shape for implantation into the cervical region a and thoracic region b.

As discussed and shown in detail below, the device 10 is configured to contain an osteogenic bone graft or bone fusion material for effectively fusing the vertebrae 5a and 5b together. Additionally, as further described and shown below, the device 10 of the present invention includes a central structural support to maintain a desired amount of separation between and/or to provide a desired amount of distraction of the vertebrae 5a and 5b and to support the patient's spinal column until the bone fusion joint forms.

Figure 4:
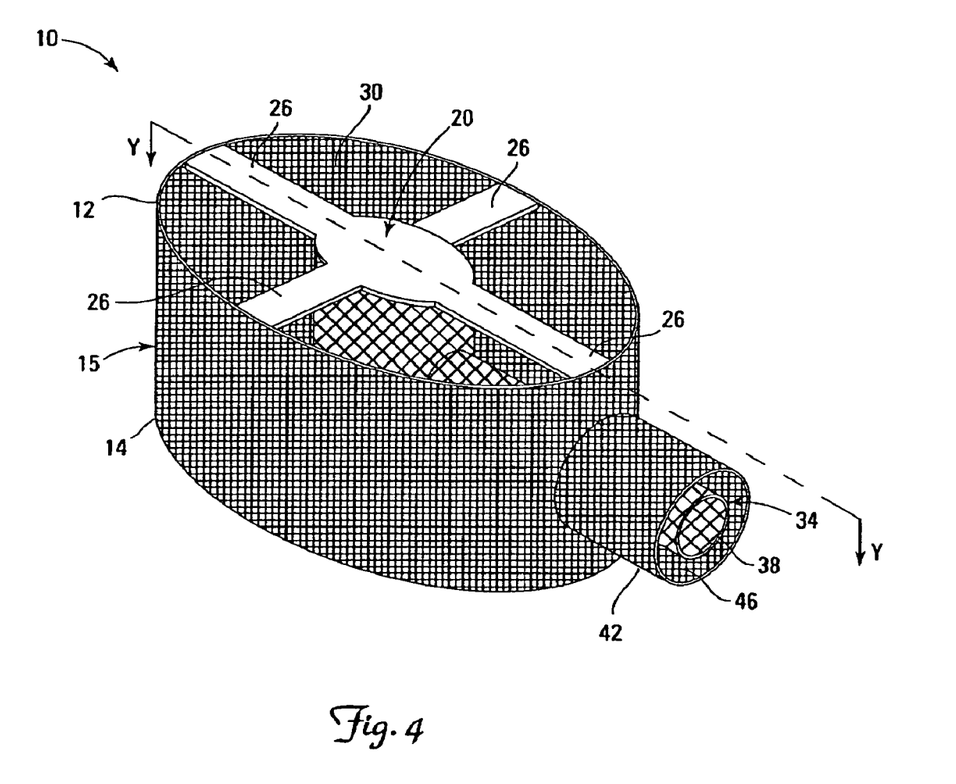
FIG. 4 depicts a perspective view of an implantable orthopedic device according to one embodiment of the present invention.

FIG. 4 is a perspective view of an implantable orthopedic device 10 according to one embodiment of the present invention. As shown in FIG. 4, the device 10 has a superior region 12 and an inferior region 14, and includes an outer wall member 15 and an inner portion 20. The outer wall member 15 and inner portion 20 are connected, in one embodiment, by at least one connecting member 26. Between the outer wall member 15 and the inner portion 20 is an outer space 30 which is open (i.e., not enclosed) in both the superior region 12 and the inferior region 14 such that, as shown and discussed in detail below, the outer space 30 is exposed to and in communication with the vertebral end plates 6, 7 (see FIGS. 2, 3) when the device 10 is placed between the vertebrae 5a and 5b as in a fusion or corpectomy procedure.

In the illustrated embodiment, the device 10 also includes an inner portal 34 extending from the inner portion 20 and including an inner portal lumen 38, and an outer portal 42 extending from the outer wall member 15 and having an outer portal lumen 46. As illustrated in FIG. 4, the inner portal 34 may be disposed within the outer portal lumen 46.

As shown and discussed in detail below, the outer space 30 is adapted to contain an osteogenic bone fusion material, such as, for example, morselized bone, which promotes and facilitates bone growth and formation of a natural rigid bone mass fusing the vertebrae 5a and 5b (see FIGS. 2-3). Additionally, as further illustrated and discussed below, the inner portion 20 operates to maintain a desired amount of separation between the vertebrae 5a and 5b to be fused, and also to structurally support and stabilize the patient's spinal column until natural bone growth fuses the vertebrae 5a and 5b.

Figure 5:
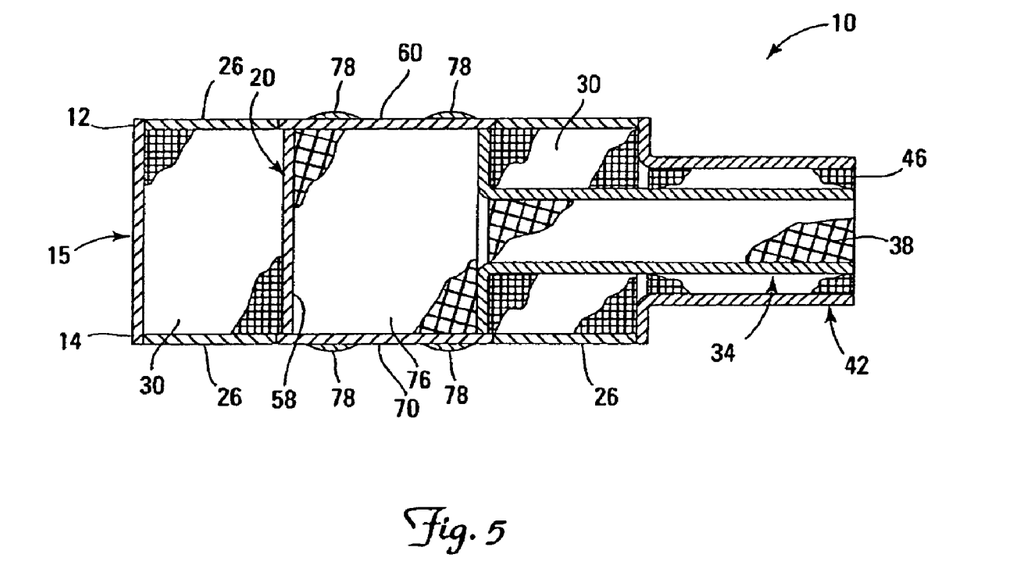
FIG. 5 depicts a cross-sectional elevation view of the device depicted in FIG. 4.

FIG. 5 is a cross-sectional elevation view of the device 10 taken along the line Y-Y in FIG. 4. As shown in FIG. 5, the inner portion 20 includes, in one embodiment, an inner wall member 58, a superior end cap 60 and an inferior end cap 70. The inner wall member 58 is attached to the superior and inferior end caps 60, 70 to define an inner compartment 76. In another embodiment, the inner portion 20 may include top and bottom members (not shown) which, along with the inner wall member 58, define the inner compartment 76 (i.e., the inner wall member 58 is not attached directly to the superior and inferior end caps 60, 70). In the embodiment illustrated in FIG. 5, the inner portal lumen 38 extends to and fluidly communicates with the inner compartment 76, and the outer portal lumen 46 extends to and fluidly communicates with the outer space 30. As further shown, the end caps 60 and 70 may include one or more projections 78, which when present may operate to engage the vertebral end plates 7 and 6, respectively, during implantation of the device 10, and/or to promote bone ingrowth and long-term positive attachment of the end caps 60, 70 to the vertebral end plates 7, 6. In the illustrated embodiment, the projections 78 are shown as generally rounded in shape, although in other embodiments, the projections 78 may have other shapes (e.g., sharp or pointed) to promote positive engagement with the vertebral end plates 6, 7.

Figure 6:
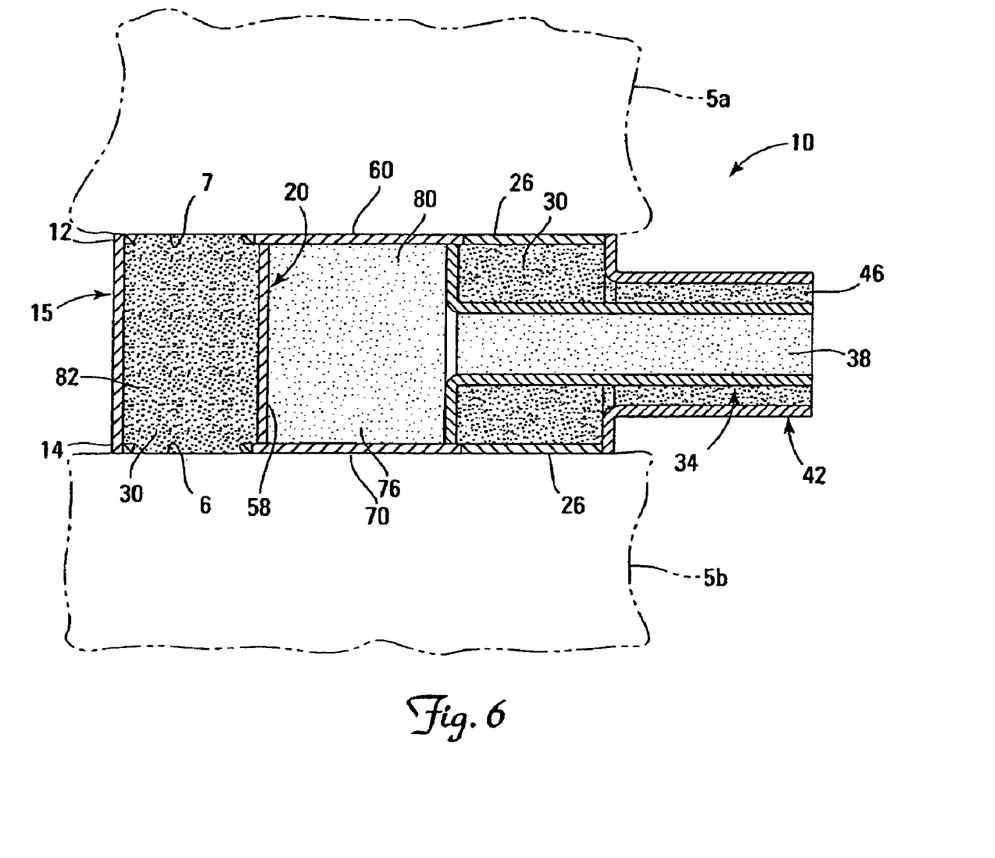
FIG. 6 depicts a partial cross-sectional elevation view of the device of FIG. 4 inserted between two vertebrae to be fused, and including inner and outer fill materials, according to one embodiment of the present invention.

FIG. 6 is a partial cross-sectional elevation view of the device 10 in use in a vertebral fusion or corpectomy procedure, in which the device 10 is inserted between two vertebrae 5a and 5b to be fused (see FIGS. 2 and 3). For illustration purposes, in FIG. 6, two of the connecting members 26 have been partially omitted. As illustrated in FIG. 6, in use, the inner compartment 76 contains an inner fill material 80, and the outer space 30 contains an outer fill material 82.

In one embodiment, the inner fill material 80 may include an injectable, in situ curable polymer or a bone cement such as polymethylmethacrylate (PMMA). In another embodiment, the inner fill material 80 may include other biocompatible materials such as, for example, injectable dental cements. Additional materials suitable for use as the inner fill material 80 will be apparent to those skilled in the art based on the foregoing. Such exemplary materials may be introduced into the inner compartment 76 in a liquid state, and subsequently cure and harden within the inner compartment 76 such that the inner portion 20 forms a substantially rigid structure.

In one embodiment, the outer fill material 82 may include an osteogenic material (i.e., a material that promotes or permits bone growth). Such osteogenic materials may include, for example, morselized bone or some other bone fusion material. In use, the outer fill material 82 may be tightly packed into and substantially completely fill the outer space 30 and, accordingly, may contact the vertebral end plates 6 and 7.

In the illustrated embodiment, the inner portal 34 and the outer portal 42 provide means for introducing the fill materials 80 and 82 into the inner compartment 76 and the outer space 30, respectively. Accordingly, in this embodiment, the inner fill material 80 is introduced into the inner compartment 76 through the inner portal lumen 38, and the outer fill material 82 is introduced into the outer space 30 via the outer portal lumen 46.

The inner portal 34 and/or the outer portal 42 may each further include means (not shown) to facilitate closure and sealing of the inner portal lumen 38 and/or the outer portal lumen 46 in order to retain the inner and outer fill materials 80 and 82 within the inner compartment 76 and the outer space 30, respectively. Such means may be integrated into the inner and outer portals portal 34 and 38, or may be integrally formed as part of the inner and outer wall members wall member 58 and 15. An exemplary closure means may be a ligature arrangement consisting of ties or draw strings, which may be tied together, drawn closed, or pulled tight like a purse string to close and seal the inner and/or outer portal lumens 34, 46. Alternatively, or additionally, the closure means may include interlocking latches, adhesives, or other fibers that can be tied and which are integrated into the inner and outer portals 34, 42, and/or the inner and outer wall members wall member 58, 15. Closure ties such as draw strings may be made of Dacron™ or suitable material. In still further embodiments, the device 10 may include a mechanical closure integrated into the inner portal 34, the outer portal 42, the inner wall member 58, and/or the outer wall member 15. Such closures may include valves (e.g., check valves, duckbill valves, flapper valves) plugs, screw caps, etc., which may be incorporated into the inner device 10 by any methods known in the art including, for example, sonic welding, sewing, or stitching.

As shown in FIG. 6, the device 10 has a size and shape suitable to at least extend between the target vertebrae 5a and 5b to be fused, with at least the end caps 60 and 70 contacting and bearing upon the end plates 7 and 6, respectively. When so positioned, because the outer space 30 is open in both the superior region 12 and the inferior region 14 of the device 10 (see FIG. 4), the outer fill material 82 can contact the vertebral end plates 6 and 7 when the device 10 is inserted between the vertebrae 5a and 5b (see FIGS. 2 and 3). When the outer fill material 82 includes an osteogenic bone fusion material such as morselized bone, the illustrated structure provides a substantially continuous bone pathway between the two vertebrae 5a and 5b, which promotes rapid bone growth therebetween and a strong fusion joint.

Additionally, location of the fused bone mass near the perimeter of the device 10 provides a fused bone joint with relatively large bending and rotational moments of inertia and, consequently, high bending and torsional rigidity. The inner portion 20, including the inner compartment 76 containing the cured inner fill material 80 such as PMMA, can maintain a desired spacing between the vertebrae 5a and 5b as determined by the physician, and operates to support the vertebrae and the spinal column prior to formation of the fused bone joint. Additionally, the device 10 can be sized such that the inner portion 20 can distract the vertebrae 5a and 5b by a desired amount.

The device 10 is generally sized and shaped to provide a maximum amount of contact area between the outer fill material 82 and the vertebral end plates 6 and 7. Although FIGS. 2 and 3 depict a device 10 utilized in the lumbar area of the spine, it should be noted that the size and shape of the device 10 may vary depending on the area of treatment and the particular vertebrae to be fused. For example, the size and shape of the device 10 for use in a cervical corpectomy procedure is generally different than the size and shape of a device 10 for use in a fusion procedure in the lumbar spine area.

Figure 7:
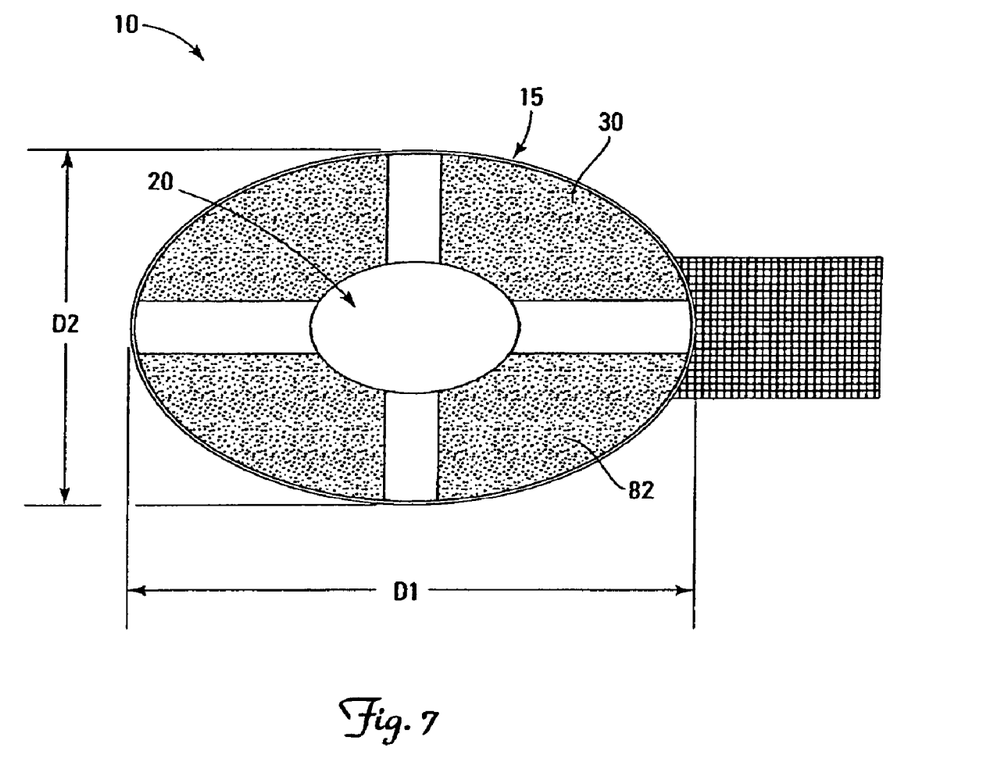
FIG. 7 is a plan view of an exemplary implantable orthopedic device according to one embodiment of the present invention.

FIG. 7 is a plan view of the device 10 according to one embodiment of the present invention. In the illustrated embodiment, from a plan view perspective, the outer wall member 15 is in the shape of a generally elliptical annular ring having a major diameter D1 and a minor diameter D2. In such an embodiment, the outer wall member 15 may have an eccentricity ratio (i.e., a ratio of the major diameter D1 to the minor diameter D2) ranging from just over 1.0 to about 3.0. In one embodiment, the eccentricity ratio of the outer wall member 15 is about 1.8. In other embodiments, the outer wall member 15 may be substantially circular—that is, having an eccentricity ratio of about 1.0. In yet other embodiments, the outer wall member 15 may have other shapes, such as, for example, substantially rectangular or irregular.

Additionally, in one embodiment, as illustrated in FIG. 7, the outer wall member 15 and inner portion 20 are sized and shaped relative to each other such that the outer space 30 is generally annular with a capacity to contain enough outer fill material 82 to provide a structurally sound bone fusion joint. In the embodiment illustrated in FIG. 7, from a plan view perspective, the inner portion 20 has substantially the same general shape (i.e., elliptical) as the outer wall member 15. In other embodiments, the inner portion 20 and the outer wall member 15 may have different shapes. For example, in one embodiment, the outer wall member 15 may have a generally elliptical shape, and the inner portion 20 may be substantially circular, and vice-versa. As an additional example, the outer wall member 15 and inner portion 20 may both be generally elliptical with different eccentricity ratios.

In one embodiment, the device 10 is expandable from a first, collapsed state to a second, expanded state by filling the inner compartment 76 with the inner fill material 80 via the inner portal lumen 38. FIGS. 4 and 5 depict the device 10 in the expanded state. In the collapsed state, the inner portion and outer wall member 15 are generally flaccid, and the device 10 has a reduced profile. As a result, in the collapsed state, the end caps 60 and 70 have a reduced separation there between to facilitate insertion between adjacent vertebrae. This also allows for a less invasive surgical insertion.

As the inner compartment is subsequently filled with the inner fill material 80 the inner compartment 76, and consequently, the inner portion 20, expand longitudinally until the expanded state is attained. If an inner fill material 80 such as those described above (e.g., PMMA) is introduced into the inner compartment 76 in a liquid state, the inner portion 20 will beneficially tend to conform to the intervertebral space in which the device 10 is implanted. Additionally, because the outer wall member 15 is attached to the inner portion 20 (as by, for example, the connecting members 26), the outer wall member 15 expands substantially concurrently with the inner portion 20. In one embodiment, one or both of the outer wall member 15 and inner wall member 58 may be configured to have a bellows construction (not shown) to facilitate expansion from the collapsed state to the expanded state.

The outer wall member 15 may be configured to be substantially taut when the device 10 is in the second or expanded state. Thus, when the device 10 is in the expanded state, and after the outer fill material 82 is packed into the outer space 30, the outer wall member 15 resists radial expansion which, in turn, creates a compressive load on the inner portion 20. This compressive load stabilizes the inner portion 20 and in turn, the patient's spinal column, until the bone fusion is complete.

In one embodiment, the outer wall member 15 and/or the inner wall member 58 may be made from a textile material. Fabrication processes for the textile material making up the outer wall member 15 and/or the inner wall member 58 may include variations and combinations of braiding, knitting and weaving. In one embodiment, one or both of the outer wall member 15 and the inner wall member 58 are made from a braided, woven, or knitted textile that has been manufactured in such a manner so as to permit longitudinal expansion when the inner fill material 80 is introduced into the inner compartment 76, but resist radial expansion and torquing. Such a textile may be made using any method known in the art to produce a textile which permits longitudinal expansion and resists radial expansion.

In another embodiment, one or both of the wall members 15, 58 may be constructed of a fiber-reinforced elastomeric composite material. In one such embodiment, the wall members 15 and/or 58 may be formed from an elastomeric polymer in which a textile material is partially or fully embedded. Any biocompatible elastomeric polymer, such as, for example, polyurethane or silicone, may be used.

In one embodiment, at least the inner wall member 58 may be made substantially non-porous to prevent leakage and loss of the inner fill material 80, particularly where the inner fill material 80 is PMMA or other comparable material introduced into the inner compartment 76 in a liquid state. Additionally, the inner wall member 58 may optionally include a flexible, non-porous internal liner (not shown) to retain the uncured, liquid inner fill material 80 within the inner compartment 76.

In one embodiment, the end caps 60 and 70 may be formed of any of several types of materials that are biocompatible or bio-inert and have good strength and rigidity/flexibility characteristics. In one embodiment, the end caps 60 and 70 are generally more rigid than the inner wall member 58 because the end caps 60 and 70 are configured to contact and apply a force to the vertebrae to be fused. One suitable type of material is a biocompatible engineering polymer, such as polyetheretherketone (PEEK™), polyaryletherketone, polyimide, polysulfone, fiber forms of polyethelene therephthalate (PET) (also known as Dacron®), solid forms of PET, polyetherimides and liquid crystalline polymers. Another such type of material is thermoplastic engineering elastomer, such as polyurethane or any other engineering elastomer having suitable stiffness. Yet another such type of material is a biocompatible metal, such as titanium or stainless steel.

In one embodiment, the end caps 60 and 70 may be semi-porous such that a controlled amount of the inner fill material 80 may pass through them to form an adhesive or mechanical connection between the end caps 60 and 70 and the vertebral end plates 7 and 6, respectively. In another embodiment, at least an outer surface of the end caps 60 and 70 may be formed of, or coated with, a porous material chosen to permit or promote bone and/or tissue ingrowth. An exemplary porous material is described in U.S. Pat. No. 5,282,861 to Kaplan, which is hereby incorporated by reference in its entirety for all that it teaches and discloses. Such materials may include porous metals, for example, open cell tantalums such as Trabecular™ Metal, and Fiber Metal (both available from Zimmer, Inc. at www.zimmer.com).

In yet another embodiment, the end caps 60 and 70 may be made from a textile material. In such embodiments, the textile material forming the end caps 60 and 70 may be the same as the textile used to form the inner wall member 58. Alternatively, the textile used to make the inner wall member 58 may be different than that used for the end caps 60 and 70. In other variations of this embodiment, different combinations of textile materials and fiber-reinforced elastomeric composite materials may be used for the inner wall member 58 and the end caps 60, 70. In still other embodiments, the end caps 60, 70 may be made from a textile material substantially impregnated with a substantially rigid engineering polymer such as, without limitation, PET and/or polyetheretherketone.

The projections 78, if present, may be made from any material that is sufficiently rigid and strong such that the projections 78, when properly shaped, can positively grip the vertebral end plate 6, 7 during implantation of the device 10.

In one embodiment, the projections 78 may be made from a biocompatible engineering polymer, such as polyetheretherketone, polyaryletherketone, polyimide, polysulfone, polyethelene therephthalate, polyetherimides and liquid crystalline polymers. The projections 78 may also be made of a thermoplastic engineering elastomer, such as polyurethane or any other engineering elastomer having suitable rigidity. Still alternatively, the projections 78 may be made from a biocompatible metal, such as titanium or stainless steel. Additionally, the projections 78 may include a coating to promote bone ingrowth. One exemplary coating material hydroxyapatite, which may promote bone ingrowth and long term positive attachment to the vertebral end plates 6, 7. Alternatively, the projections 78 may be made of a porous bone ingrowth material, such as Trabecular™ Metal and Fiber Metal as described above. When made from such materials, the projections 78 advantageously provide both initial attachment to the vertebral end plates 6, 7 and also long term positive attachment of the end caps 60, 70 to the vertebral end plates 7 and 6, respectively, through bone ingrowth.

The connecting members 26 may be made from the same or similar materials as the end caps 60, 70. Alternatively, the connecting members 26 may be made from a textile material such as those used for the outer and inner wall members 15 and 58. A biocompatible elastomeric material, either fiber-reinforced or non-reinforced, may also be used for the connecting members 26. Any method of attachment known in the art (e.g., stitching, adhesives, etc.) may be used to attach the connecting members 26 to the outer wall member 15 and the end caps 60 and 70 (or other region of the inner portion 20).

Figure 8A:
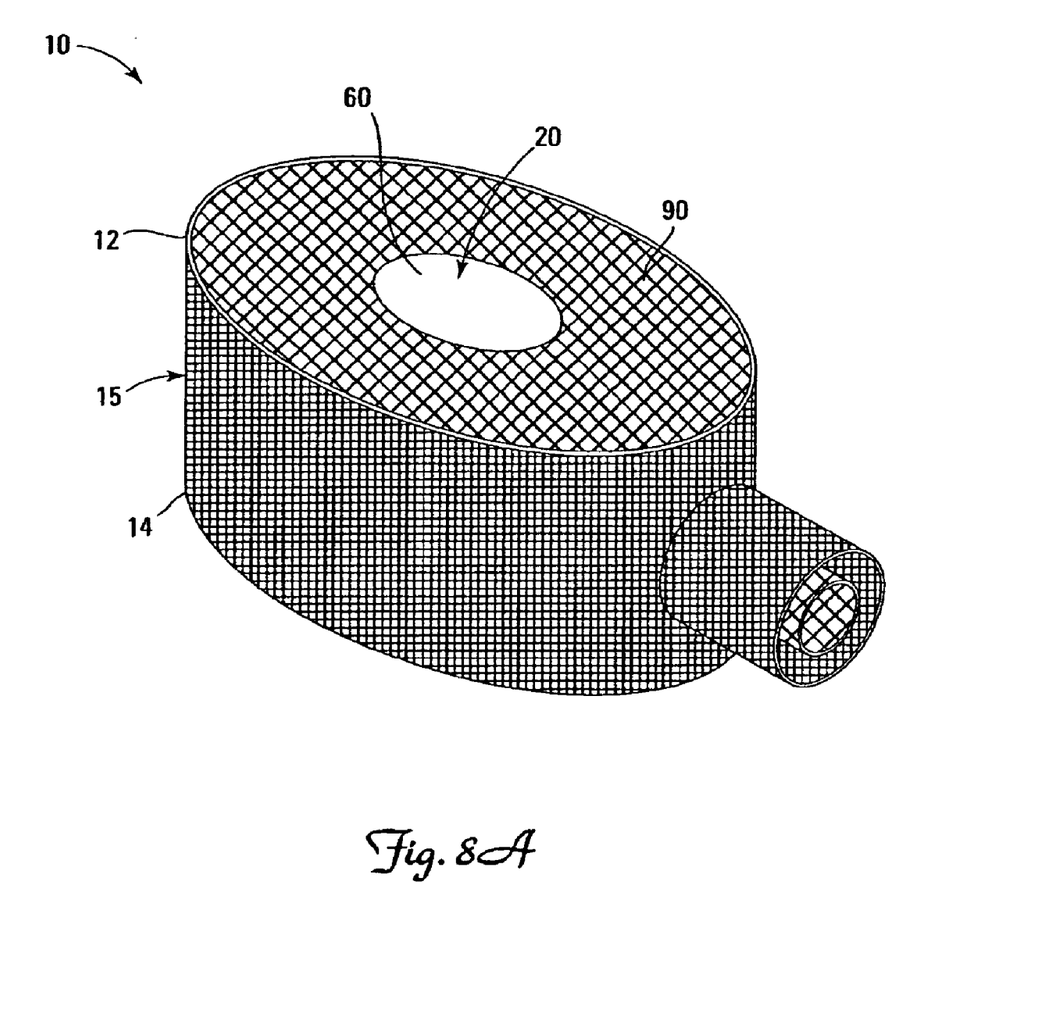
FIGS. 8A and 8B depict alternative embodiments of an implantable orthopedic device according to the present invention.

FIG. 8A is a perspective view of an alternative embodiment of the device 10, in which the connecting members 26 in the superior region 12 are replaced by a connecting ring 90. As illustrated, the connecting ring 90 is attached to the outer wall member 15 around substantially the entire circumference of the outer wall member 15. Similarly, the connecting ring 90 is also attached to substantially the entire periphery of the superior end cap 60.

In such embodiments, the connecting ring 90 is adapted to substantially retain the outer fill material 82, such as morselized bone or other osteogenic material, but not significantly interfere with bone fusion between the vertebrae 5a and 5b. In one embodiment, the connecting ring 90 may be constructed of a textile material configured to facilitate bone fusion there through. In another embodiment, the connecting ring 90 may be made from a porous bone ingrowth materials such as Trabecular™ Metal and Fiber Metal (available from Zimmer, Inc. at www.zimmer.com) described above. In yet another embodiment, the connecting ring 90 may be made from a biocompatible elastomeric material, which may or may not be fiber-reinforced. In any of the foregoing embodiments, the connecting ring 90 may include perforations or openings (not shown) to permit direct communication and contact between the outer fill material 82 and the vertebral end plate 7 when used in a fusion procedure. As will be appreciated by those of ordinary skill in the art, although not shown in FIG. 8A, the connecting members 26 in the inferior region 14 may also be replaced by another connecting ring 90 which may also be connected to the outer wall member 15 and the inner portion 20 in the same manner as described above with respect to the superior region 12.

Figure 8B:
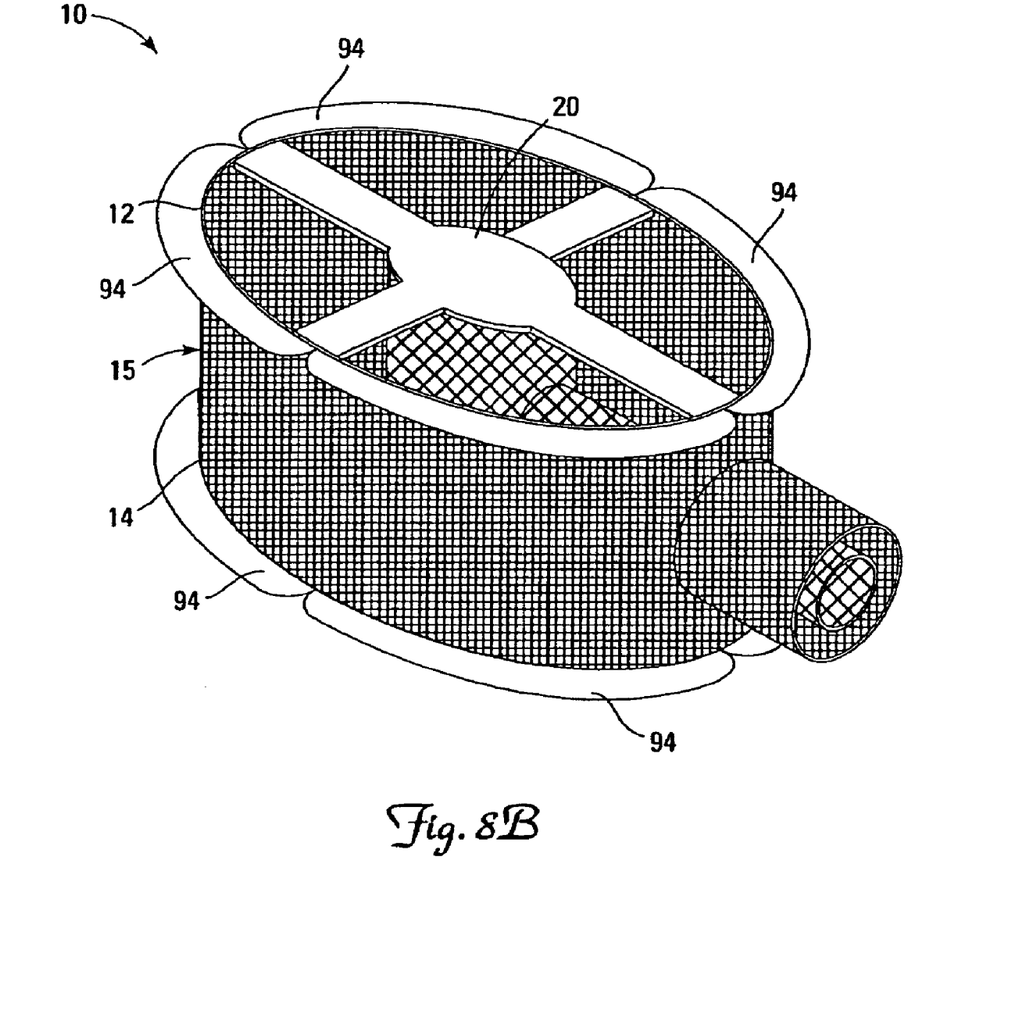

FIG. 8B is a perspective view of yet another embodiment of the device 10 including flaps 94 extending from the outer wall member 15 in both the superior and inferior regions 12 and 14 The flaps 94 may be folded or extended upward (in the superior region 12) and downward (in the inferior region 14) such that when the device 10 is positioned between the vertebrae 5a and 5b, the flaps 94 are adjacent to and can be tacked to the vertebrae 5a, 5b. The flaps 94 thus operate to hold the device 10 in a desired position during the implantation process, and also to assist in retaining the outer fill material 82 inside the outer space 15 until bone fusion occurs. The flaps 94 may be made from the same material as the outer wall member 15, but this is not a requirement. To the contrary, any biocompatible, flexible material may be used for the flaps 94, which may be attached to the outer wall member 15 using any methods known in the art (e.g., stitching, adhesives, bone screws, bone anchors).

Figure 9:
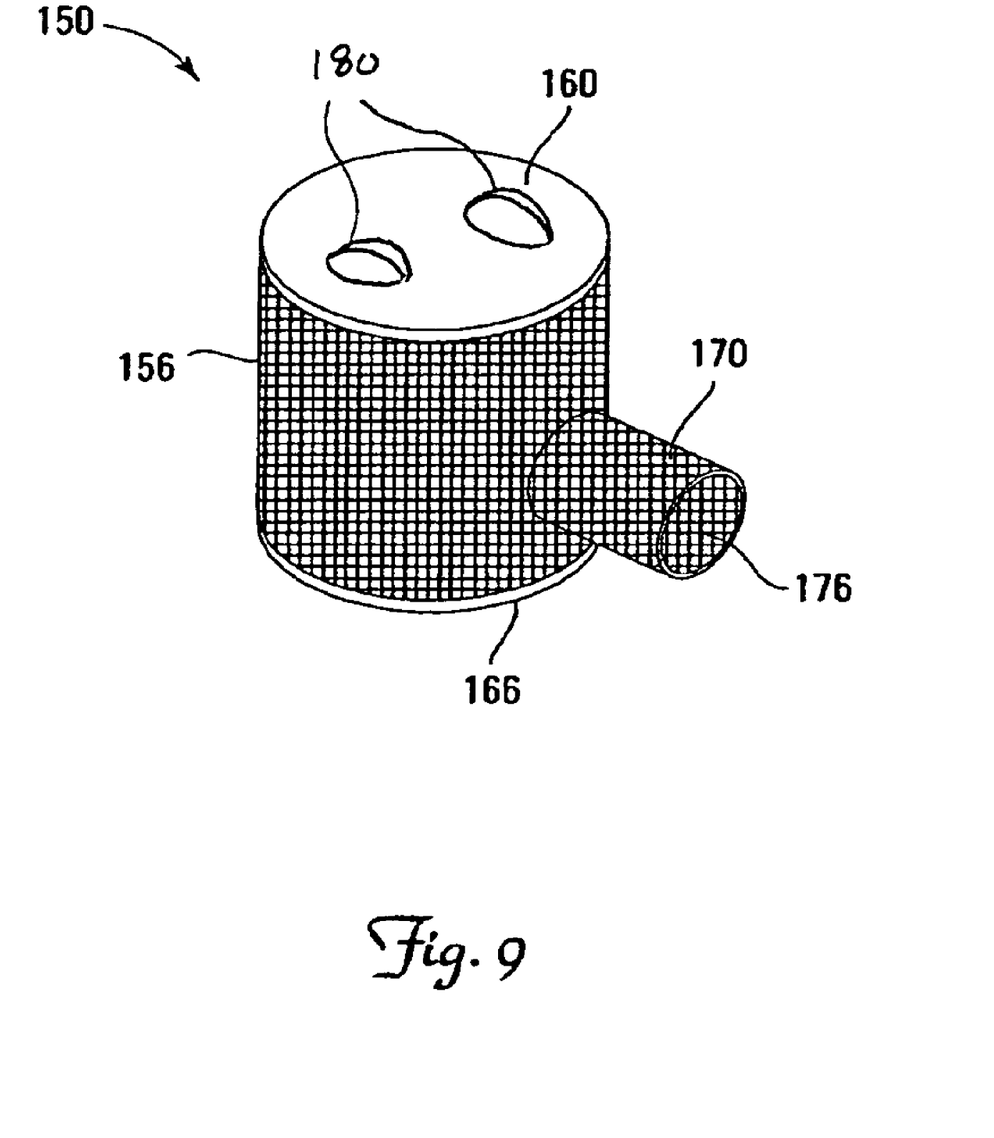
FIG. 9 depicts another embodiment of an implantable orthopedic device according to the present invention.

FIG. 9 depicts a perspective view of an implantable orthopedic device 150 according to another embodiment of the present invention. The device 150 may advantageously be used to facilitate fusion of vertebrae 5a and 5b that are adjacent one another (see FIG. 2). In such a procedure, only the nucleus of the intervertebral disc 8 is substantially or completely removed, and the outer portion or annulus of the disc 8 is left substantially intact. As shown in FIG. 9, the device 150 is shaped like a tubular sleeve and includes a side wall 156, a pair of end caps 160 and 166, and a portal 170 having a lumen 176 therethrough. The side wall 156 and the end caps 160 and 170 define a compartment (not shown) for containing a fill material such as PMMA. The lumen 176 communicates with and facilitates the introduction of the fill material into the compartment.

In general, the device 150 is constructed and configured to operate in a manner substantially similar to the inner portion 20 of the device 10 described in detail above. For example, the side wall 156 may be constructed of textile materials similar to those used for the inner wall member 58 of the device 10. Similarly, the end caps 160 and 166 may be constructed of materials similar to those used for the end caps 60 and 70 of the device 10. As shown, at least one of the end caps 160 and 166 may include one or more projections 180 which are substantially similar in both construction and operation as the projections 78 discussed above.

In operation, when filled with an appropriate fill material, the device 150 is adapted to maintain a desired amount of spacing between and/or provide a desired amount of distraction of the adjacent vertebrae to be fused, similar to the operation of the inner portion 20 containing the cured inner fill material 80 of the device 10 described above. A bone graft or bone fusion material may then be packed around the outside of the device. Additionally, in one embodiment, as discussed in more detail below, the outer portion, or annulus, of the intervertebral disc 8 is left intact and operates to contain the bone fusion material in much the same way as the outer wall member 15 of the device 10 described above.

Figure 10:
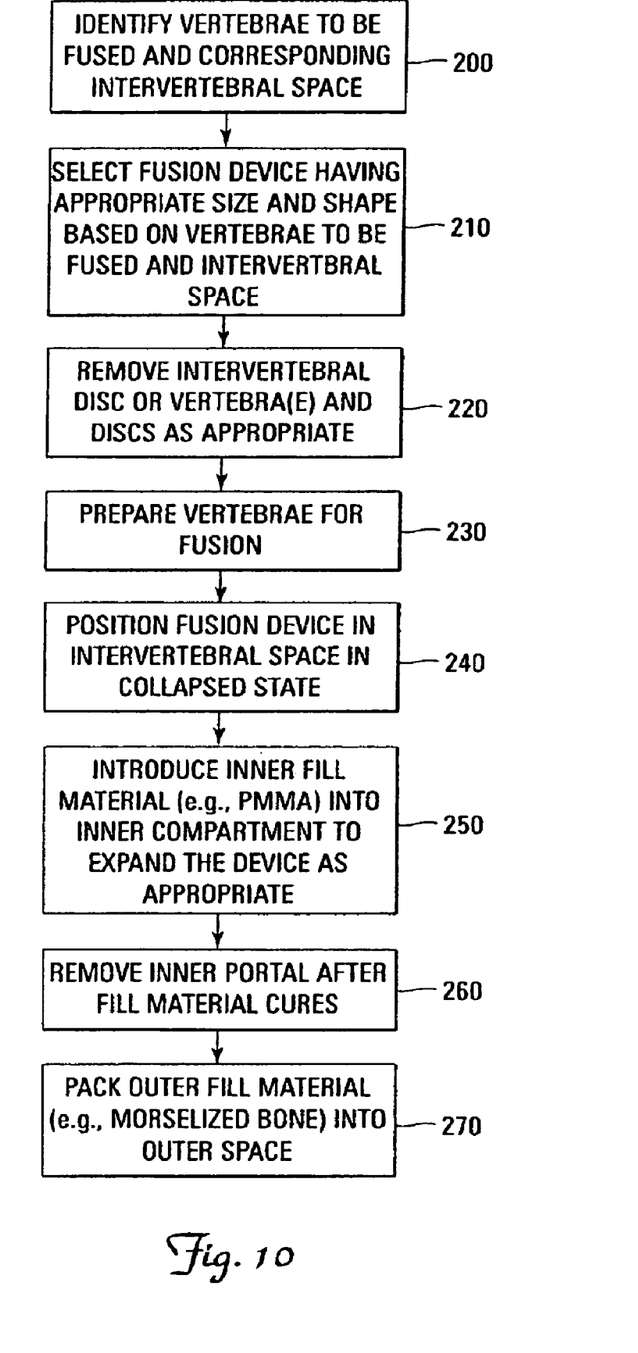
FIG. 10 is a flowchart describing a fusion procedure utilizing an implantable orthopedic device according to one embodiment of the present invention.

FIG. 10 illustrates a method of performing a vertebral fusion procedure utilizing the device 10 (FIG. 2) according to one embodiment of the present invention. As shown in FIG. 10, the two vertebrae 5a and 5b to be fused are identified by a physician, and this, in turn defines the intervertebral space into which the device 10 is to be inserted (200). In one embodiment, the vertebrae 5a, 5b to be fused may be adjacent one another (see FIG. 2). Alternatively, as in a corpectomy procedure (see FIG. 3), the vertebrae 5a, 5b to be fused may naturally be separated by one or more intervening vertebra and adjacent intervertebral discs 8 which must be removed by the surgeon. Based on the specific vertebrae 5a and 5b to be fused and the resulting intervertebral spacing, an appropriately sized and shaped device 10 is selected and provided (210). The area of treatment is then accessed using techniques and instruments known in the art, and, depending on the vertebrae chosen for fusion, the intervertebral disc 8 or one or more vertebra 5 and adjacent intervertebral discs 8 are removed (220). The vertebra 5a, 5b to be fused are then prepared for implantation of the device 10 and subsequent bone fusion, according to standard procedures known to those in the art (230).

In one embodiment, the physician positions the patient and creates a desired spacing between the vertebrae 5a and 5b to be fused before inserting the device 10 into the intervertebral space. The device 10, in the collapsed state, may then be positioned in the space between the vertebra 5a, 5b to be fused, such that when the device 10 is in the expanded state, the end caps 60, 70 will contact the vertebral end plates 7, 6, respectively, and the outer space 30 will communicate with the end plates 6, 7 (240). The inner fill material 80, such as PMMA, may then be introduced into the inner compartment 76 via the inner portal lumen 38, causing the inner portion 20 and the device 10 in general to attain its expanded state, such that the end caps 60, 70 are in contact with the vertebral end plates 7, 6, respectively. In one embodiment, the physician may use the appropriately sized device 10, and in particular, the inner portion 20, to distract the vertebrae 5a, 5b by a desired amount by filling the inner compartment 76 with the inner fill material 80 (250).

In one embodiment, liquid PMMA or other comparable inner fill material 80 may be introduced into the inner compartment 76 via a pump (not shown) coupled to the inner portal 34. A syringe or other manual device may also be used to inject the inner compartment 76 with the inner fill material 80. Pressure within the inner compartment 76 is maintained until the inner fill material 80 cures and hardens to create a support capable of maintaining the desired amount of spacing between the vertebrae 5a and 5b, and also of supporting the patient's spinal column until the natural bone fuses. For example, where the inner fill material 80 is pumped into the inner compartment 76, the pump may remain coupled to the inner portal lumen 38 and configured to maintain a desired internal pressure in the inner compartment 76. Alternatively, or additionally, the inner portal lumen 38 may be sealed using any of the closure means described above, if present.

After the inner fill material 80, such as PMMA, is cured and hardened, and the inner portion 20 is capable of supporting the patient's spinal column and/or maintaining the desired amount of separation between the vertebrae 5a, 5b, the inner portal 34 may optionally be totally or partially removed (260) by any means known in the art (e.g., scissors, scalpel). Removal of the inner portal 34 may facilitate introduction of the outer fill material 82 into the outer space 30, particularly where the inner portal 34 is disposed within the outer portal lumen 46.

If present, the flaps 94 may be extended and tacked to the vertebrae 5a and 5b prior to introducing the outer fill material 82 into the outer space 30. In such embodiments, the flaps 94 operate to inhibit migration of the outer fill material 82 from the outer space 30 at the interface between the outer wall member 15 and the vertebral end plates 6 and 7. The outer fill material 82, such as morselized bone or other osteogenic bone fusion material, is then introduced and packed into the outer space 30 via the outer portal lumen 46 (270). The outer fill material 56 may be introduced into the outer space 30 using any method known in the art (e.g., large bore syringe, spatula, tamp and cannula). The outer portal lumen 46 may then be closed and sealed using any of the closure means described above, thereby retaining the outer fill material 56 in the outer space 30.

In another embodiment of a method utilizing the devices 10 or 150 of the present invention, only a desired amount of the central portion or nucleus of the intervertebral disc 8 is removed, using known techniques and surgical instruments.

In some embodiments, only a portion of the disc nucleus may be removed. In other embodiments, the entire nucleus may be removed as dictated by the physician based on the needs of the patient. The outer portion or annulus of the disc 8 may be left substantially intact, thus forming a cavity between the vertebrae 5a, 5b substantially enclosed by the remaining disc annulus. When left intact, the disc annulus may beneficially operate to support the device 10 or 150, and accordingly, the bone fusion joint, prior to fusion. Additionally, when using the device 150 to facilitate vertebral fusion, the substantially intact disc annulus operates to retain the bone fusion material until fusion is complete.

The device 10 or 150 may then be positioned in the cavity between the vertebrae 5a, 5b. Where the device 10 is used, the implantation and fusion procedure may proceed as described above. Where the device 150 is used in this embodiment, a fill material (e.g., PMMA) is then injected into the device 150 in the same manner as that described above with respect to filling the inner compartment 76 of the device 10. An osteogenic material (e.g., morselized bone) is then packed into the cavity between the vertebrae 5a and 5b and around the device 150, and is substantially retained therein by the remaining disc annulus material.

Various modifications and additions may be made to the exemplary structures and steps discussed without departing from the scope of the present invention. Various combinations, permutations, and rearrangements of those structures and steps may similarly be made without departing from the scope of the present invention. Accordingly, the scope of the present invention is intended to embrace all such alternatives, modifications, permutations and variations as fall within the scope of the claims, together with all equivalents thereof.

We claim:

1. An implantable orthopedic device for implantation between opposed vertebral end plates of a pair of vertebrae, the device comprising: an inner portion including a pair of spaced-apart end caps and an inner wall member there between, wherein the end caps and the inner wall member define a compartment; an outer wall member disposed about and coupled to the inner portion, wherein separation between the outer wall member and the inner portion defines an outer space, wherein at least a portion of each end cap is spaced from the outer wall member; and a first portal in fluid communication with the compartment and isolated from the outer space, and a second portal in fluid communication with the outer space and isolated from the compartment; wherein the device has a size and shape such that the device can extend between the opposed vertebral end plates such that the end caps and the outer space are in contact with the vertebral end plates.

2. The device of claim 1 further comprising a first fill material disposed within the compartment.

3. The device of claim 2 wherein the first fill material comprises a curable polymer.

4. The device of claim 2 wherein the first fill material comprises polymethylmethacrylate.

5. The device of claim 1 further comprising a second fill material disposed within the outer space.

6. The device of claim 5 wherein the second fill material comprises an osteogenic material.

7. The device of claim 1 wherein at least one of the outer or the inner wall members is made substantially from a textile material.

8. The device of claim 7 wherein the textile material is configured to permit longitudinal expansion and resist radial expansion of the at least one of the outer or inner wall members.

9. The device of claim 8 wherein the textile material comprises a braided, woven or knitted textile.

10. The device of claim 1 wherein at least one of the outer or inner wall members is made substantially from a fiber-reinforced elastomeric composite material.

11. The device of claim 1 wherein the end caps are made substantially from a material selected from the group consisting of polyetheretherketone, polyaryletherketone, polyimide, polysulfone, polyethelene therephthalate, polyetherimides, polyurethane, and liquid crystalline polymers.

12. The device of claim 1 wherein the end caps are made substantially from a bone ingrowth material.

13. The device of claim 12 wherein the bone ingrowth material comprises an open cell tantalum material.

14. The device of claim 1 wherein the end caps are made substantially from a biocompatible metal.

15. The device of claim 1 wherein the end caps are made substantially from a material selected from the group consisting of textiles and fiber-reinforced elastomeric composites.

16. The device of claim 1 wherein at least one of the end caps comprises at least one bone engaging projection.

17. The device of claim 16 wherein the at least one bone engaging projection is made substantially from a bone ingrowth material.

18. The device of claim 1 wherein the outer wall member comprises an extendable member adapted to be attached to one of the vertebrae.

19. The device of claim 1 wherein the inner portion is adapted to expand longitudinally from a first state to a second state upon an introduction of a first fill material into the compartment, and wherein the outer wall member is adapted to expand longitudinally substantially concurrently with the inner portion upon the introduction of the first fill material into the compartment, and wherein the device is configured to maintain a desired amount of spacing between the opposed vertebral end plates when the device is in the second state.

20. The device of claim 19 wherein the device is further configured to distract the opposed vertebral end plates by a desired amount.

21. The device of claim 1 wherein the first and second portals are coaxial.

22. An implantable orthopedic device for implantation between opposed vertebral end plates of a pair of vertebrae, the device comprising: a pair of spaced apart end caps, wherein at least one of the end caps is configured to be substantially rigid; an inner wall member extending between the end caps, wherein the inner wall member and the end caps define a compartment; a curable polymer fill material disposed within and substantially filling the compartment, wherein the device has a size and shape such that it can extend between the opposed vertebral end plates such that at least the end caps can be in contact with the vertebral end plates; an outer wall member connected to the pair of end caps by one or more connecting members, wherein an outer space is formed between the outer wall member and the inner wall member, wherein the outer space is exposed to opposed vertebral end plates upon insertion of the device between two vertebral end plates; and a portal in fluid communication with the compartment.

* * * * *